(12) United States Patent
Chang et al.

(10) Patent No.: US 9,207,161 B2
(45) Date of Patent: Dec. 8, 2015

(54) FILM ADHESION DETECTION DEVICE AND METHOD THEREOF

(71) Applicant: St. John's University, New Taipei (TW)

(72) Inventors: Rwei-Ching Chang, New Taipei (TW); Tsai-Cheng Li, New Taipei (TW); Hsi-Ting Hou, New Taipei (TW); Chen-Pei Yeh, New Taipei (TW); Fa-Ta Tsai, New Taipei (TW)

(73) Assignee: ST. JOHN'S UNIVERSITY, New Taipei (TW)

( * ) Notice: Subject to any disclaimer, the term of this patent is extended or adjusted under 35 U.S.C. 154(b) by 234 days.

(21) Appl. No.: 14/017,396

(22) Filed: Sep. 4, 2013

(65) Prior Publication Data

US 2015/0059488 A1    Mar. 5, 2015

(51) Int. Cl.
*G01N 19/04* (2006.01)

(52) U.S. Cl.
CPC ........ *G01N 19/04* (2013.01); *G01N 2203/0053* (2013.01)

(58) Field of Classification Search
CPC ................................. G01N 19/04; G01N 3/56
USPC ..................................................... 73/150 A, 7
See application file for complete search history.

(56) References Cited

U.S. PATENT DOCUMENTS

| | | | |
|---|---|---|---|
| 3,985,026 A * | 10/1976 | Griffin et al. | 73/150 R |
| 4,065,964 A * | 1/1978 | Cunningham | 73/150 A |
| 5,176,028 A * | 1/1993 | Humphrey | 73/150 A |
| 5,458,729 A * | 10/1995 | Galchefski et al. | 156/566 |
| 5,546,797 A * | 8/1996 | Dutta et al. | 73/150 A |
| 5,765,431 A * | 6/1998 | Hupf | 73/7 |
| 5,804,706 A * | 9/1998 | Williston | 73/78 |
| 6,078,387 A * | 6/2000 | Sykes | 356/244 |
| 6,301,971 B1 * | 10/2001 | Sykes | 73/827 |
| 6,428,233 B1 * | 8/2002 | Clark et al. | 401/196 |
| 6,502,455 B1 * | 1/2003 | Gitis et al. | 73/150 A |
| 6,520,004 B1 * | 2/2003 | Lin | 73/81 |
| 6,584,858 B1 * | 7/2003 | Miyazawa et al. | 73/827 |
| 6,981,408 B1 * | 1/2006 | Madanshetty | 73/150 A |
| 7,272,969 B2 * | 9/2007 | Shinohara et al. | 73/7 |
| 7,302,831 B2 * | 12/2007 | Moyse et al. | 73/81 |
| 7,347,768 B1 * | 3/2008 | Drew | 451/38 |
| 7,448,941 B2 * | 11/2008 | Drew | 451/8 |
| 7,628,065 B2 * | 12/2009 | Yang et al. | 73/150 A |

(Continued)

FOREIGN PATENT DOCUMENTS

EP    0 434 633 B1 *    9/1994

*Primary Examiner* — Max Noori
*Assistant Examiner* — Tran M Tran
(74) *Attorney, Agent, or Firm* — McClure, Qualey & Rodack, LLP

(57) ABSTRACT

A film adhesion detection device comprises: a testing member, which comprises: a carrier, which is on the testing member and is capable of vacuum suction to adsorb a testing sample, the carrier can raise, move, rotate, and position; a testing cutting tool, which is on the testing member and is capable of dismantling from the testing member; a counterpoise, which is on the testing cutting tool to provide a suitable weight to the testing cutting tool according to the strength and thickness of the testing sample; and a tape adhesion testing device, which is on the testing member and has a tape-outputting wheel, a counterpoise and a tape recovery wheel, the tape adhesion testing device provides a suitable adhesion force to the testing sample via the counterpoise, the tape recovery wheel tears off a tape after the tape is on a film.

3 Claims, 16 Drawing Sheets

(56) References Cited

U.S. PATENT DOCUMENTS

| | | |
|---|---|---|
| 7,730,761 B2 * | 6/2010 | Gregory et al. ..................... 73/7 |
| 7,913,552 B2 * | 3/2011 | Himmelbauer et al. ..... 73/150 A |
| 7,997,118 B2 * | 8/2011 | Mecca et al. ........................ 73/7 |
| 8,215,163 B2 * | 7/2012 | Zhang ......................... 73/150 A |
| 8,438,901 B2 * | 5/2013 | Gregory et al. ..................... 73/7 |
| 8,549,891 B2 * | 10/2013 | Ryan et al. .......................... 73/7 |
| 8,667,844 B1 * | 3/2014 | Broadbent et al. ............... 73/588 |
| 8,714,025 B2 * | 5/2014 | Lilley et al. ..................... 73/788 |
| 8,813,553 B2 * | 8/2014 | Hoshino ..................... 73/150 A |
| 2006/0171579 A1 * | 8/2006 | Lee et al. ....................... 382/141 |
| 2013/0186172 A1 * | 7/2013 | Biskeborn et al. ................. 73/7 |

* cited by examiner

FILM ADHESION DETECTION DEVICE AND METHOD THEREOF

BACKGROUND OF THE INVENTION

1. Field of the Invention

The present invention generally relates to a film adhesion detection device and a method for detecting the adhesion of a film using the film adhesion detection device, more particularly to a device that integrates a device for scratch test with a device for tape-tearing test in order to automatically detect the adhesion force of a film for promoting accuracy and convenience and a method thereof.

2. Description of the Related Art

Film is widely used in various industries in recent years because of its outstanding performance and stable quality, hence it has become a very important manufacturing technology. However, in deposition processes, accumulated residual stress may easily affect the film adhesion properties, so for the film being with excellent performance and stable quality conditions, the film adhesion test is even more important.

The method of detecting a film adhesion is broadly applied, and the most commonly used test standard is ISO 2409:2013 or ASTM D 3359 09E2. As shown in FIG. 1, a cross-cut knife is manually operated to scratch a plurality of vertical and horizontal grid lines on the surface of a film. Since the cross-cut knife has ten sets of tool blades, so total is one hundred cells produced. And then a tape is adhered to the surface of the film and after a pressure is applied and some time is passed, the tape can be peeled off, a testing staff may determine the level of the film adhesion according to the test standard. The scratch test by the cross-cut knife and the subsequent tearing test are both manually operated, however due to different forces with different people and with no standardized norms to be followed, even there is only one person to operate, different times of operations may cause different experimental conditions.

Currently available automatic scratch devices are to act as agent, which web address is tw.ttnet.net. Although this device can automatically scratches, but can only do a first scratch, and there is another need that the sample is manually turned 90 degrees for transverse scratches, and the most important action may also need to rely on a manual adhering act.

Obviously, the cross-cut knife scratch test and the tearing test are still having shortcomings, hence to integrate the cross-cut knife scratch test with the tearing test and using a counterpoise to control an applied force will tremendously promote the accuracy of the test.

Further, an R.O.C. patent, which application number is 90121558, patent number is 505785 and is titled as method and apparatus for measuring thin film adhesion force, and another R.O.C. patent, which application number is 95209461, patent number is M301339, and is titled as paint hardness tester, both focus to improve the problem of unbalanced force in scratch test, but are not related to a device for integrating an automatic scratch test and a tape-tearing test provided by the present invention.

SUMMARY OF THE INVENTION

The main objective of the present invention is to provide a film adhesion detection device and a method thereof in order to solve the shortcoming of the inaccuracy caused by too many people operating a system while a prior film adhesion test is proceeded. The present invention integrates scratch tests and a tape-tearing test, that is, the present invention comprises a device for scratch test and a device for tape-tearing test in order to detect a continuity film adhesion for accuracy and convenience.

The second objective of the present invention is to figure out an unbalanced applied force in prior arts, so as to increase the added values of the device for scratch test.

A film adhesion detection device comprises: a testing member, which comprises: a carrier, which is on the testing member and is capable of vacuum suction in order to adsorb a testing sample, the carrier is able to raise up and down, move back and forth, rotate, and position; a testing cutting tool, which is on the testing member and is capable of dismantling from the testing member, and has a plurality of sets of knives; a counterpoise, which is on the testing cutting tool in order to provide a weight to the testing cutting tool, the counterpoise is able to apply a suitable weight to the testing cutting tool according to the strength and thickness of the testing sample, therefore the testing cutting tool can averagely apply a force on the testing sample for accuracy; and a tape adhesion testing device, which is on the testing member and has a tape-outputting wheel, a counterpoise and a tape recovery wheel, the tape adhesion testing device provides a suitable adhesion force to the testing sample by means of the counterpoise, the tape recovery wheel tears off a tape after the tape is pasted on a film.

A method for detecting the adhesion of a film using a film adhesion detection device comprising the steps of: (S1) using a sample-loading device to dispose a testing sample on a carrier of a testing member of a film adhesion detection device; (S2) lowering down the carrier; (S3) moving the carrier to a testing cutting tool; (S4) raising up the carrier; (S5) using a heating device to heat the testing sample and moving the carrier for proceeding an X-axis scratch test, wherein a first counterpoise applies a suitable weight to the testing cutting tool according to the strength and thickness of the testing sample; (S6) stopping from moving the carrier and lowering down the carrier after the X-axis scratch test; (S7) rotating the carrier for an angle; (S8) raising up the carrier; (S9) reversely moving the carrier for proceeding a Y-axis scratch test, wherein a first counterpoise applies a suitable weight to the testing cutting tool according to the strength and thickness of the testing sample; (S10) continuously moving the carrier (9) after the Y-axis scratch test; (S11) the carrier going to a tape adhesion testing device that connects with a tape-outputting wheel, a second counterpoise and a tape recovery wheel, the second counterpoise providing a suitable weight to the tape adhesion testing device for providing the testing sample a suitable adhesion force, thus the tape averagely sticking on the testing sample, meanwhile, the tape recovery wheel tearing off the tape and recycling the tape; (S12) finishing the sticking and tearing, and stopping the carrier; and (S13) using the sample-loading device to unload the testing sample from the carrier and checking the tearing condition of the film of the testing sample, then determining the adsorbing condition of the film.

Other and further features, advantages, and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms. Like numerals refer to like parts throughout the disclosure.

BRIEF DESCRIPTION OF THE DRAWINGS

The objects, spirits, and advantages of the preferred embodiments of the present invention will be readily understood by the accompanying drawings and detailed descriptions, wherein.

DETAILED DESCRIPTION OF THE INVENTION

Following preferred embodiments and figures will be described in detail so as to achieve aforesaid objects.

Figure 1:
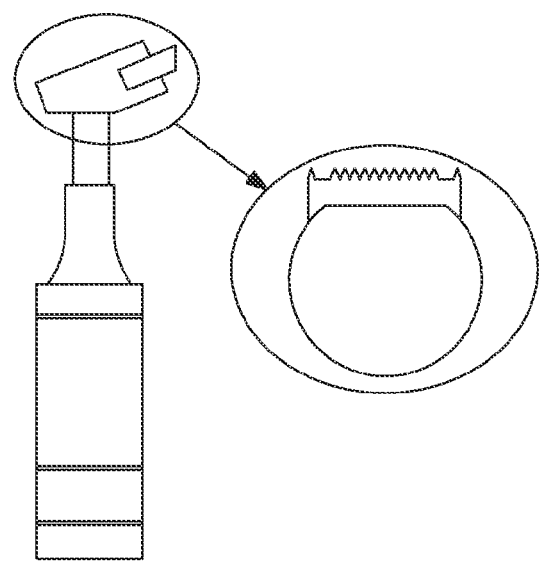
FIG. 1 illustrates a schematic view of a cross-cut knife in prior art.
Figure 2:
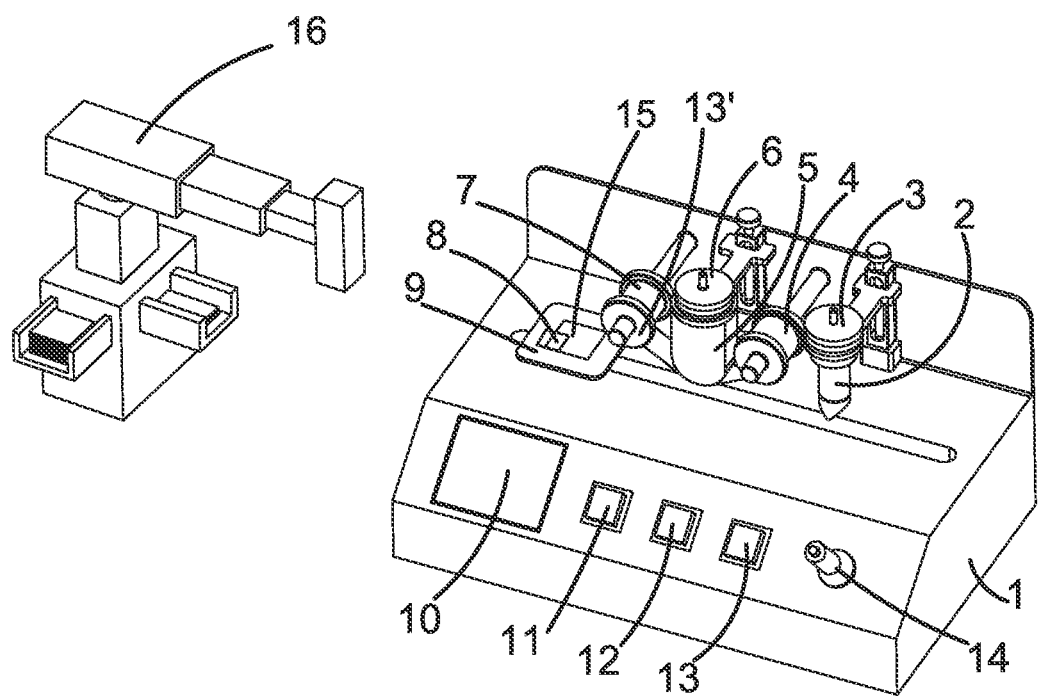
FIG. 2 illustrates a schematic view of the film adhesion detection device of the present invention.

With reference to FIG. 2, which illustrates a schematic view of the film adhesion detection device and the method thereof of the present invention. A testing member 1 provided by the present invention has a testing cutting tool 2, a first counterpoise 3, a tape-outputting wheel 4, a tape adhesion testing device 5, a second counterpoise 6, a tape recovery wheel 7, a carrier 9, a screen 10 for moving information, a power switch 11, a vacuum adsorption button 12, a start button 13, a handhold rod 14 for the carrier 9 raising up and down, moving back and forth, and rotating, a heating device 15, and a sample-loading device 16. Through the carrier 9, the vacuum adsorption button 12 and the handhold rod 14, a testing sample 8 may be adsorbed on the carrier 9, and then be moved toward right in FIG. 2 to the testing cutting tool 2, but the heating device 15 is installed on the carrier 9 for heating the testing sample 8. Then, the first counterpoise 3 with a proper weight is applied to the testing cutting tool 2 in order to proceed an X-axis scratch test and a Y-axis scratch test. After that, the testing sample 8 goes to the tape adhesion testing device 5 that connects with the tape-outputting wheel 4, the second counterpoise 6 and the tape recovery wheel 7. The second counterpoise 6 provides a suitable weight to the tape adhesion testing device 5 for providing the testing sample 8 a suitable adhesion force, thus a tape 13' can averagely stick on the testing sample 8. Meanwhile, the tape recovery wheel 7 tears off the tape 13' and recycle the tape 13'. Hence, the testing sample 8 is taken off so as to check the adsorbing condition of a film.

Figure 3:
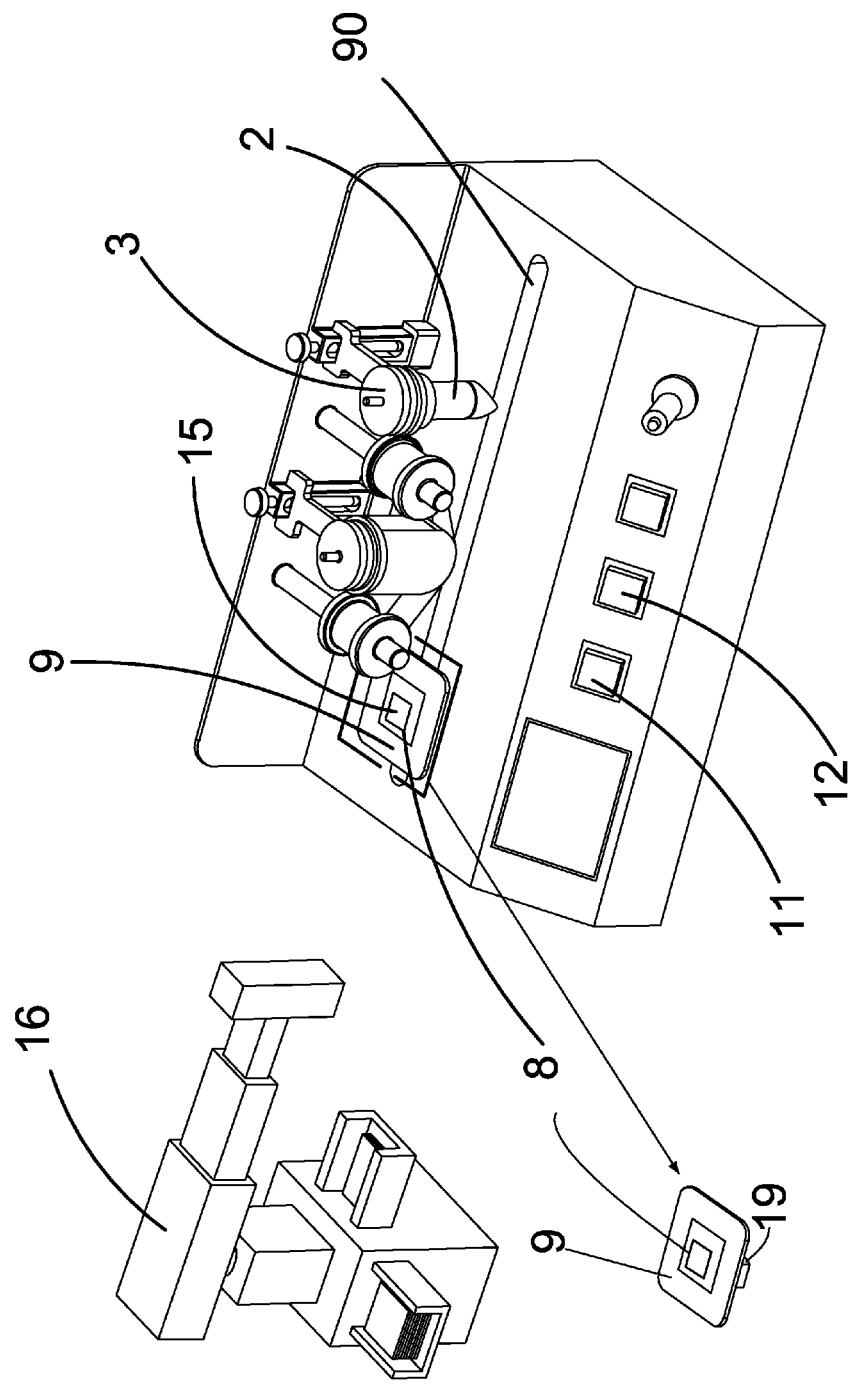
FIG. 3 illustrates a schematic view of manually loading a testing sample of the film adhesion detection device of the present invention.
Figure 4:
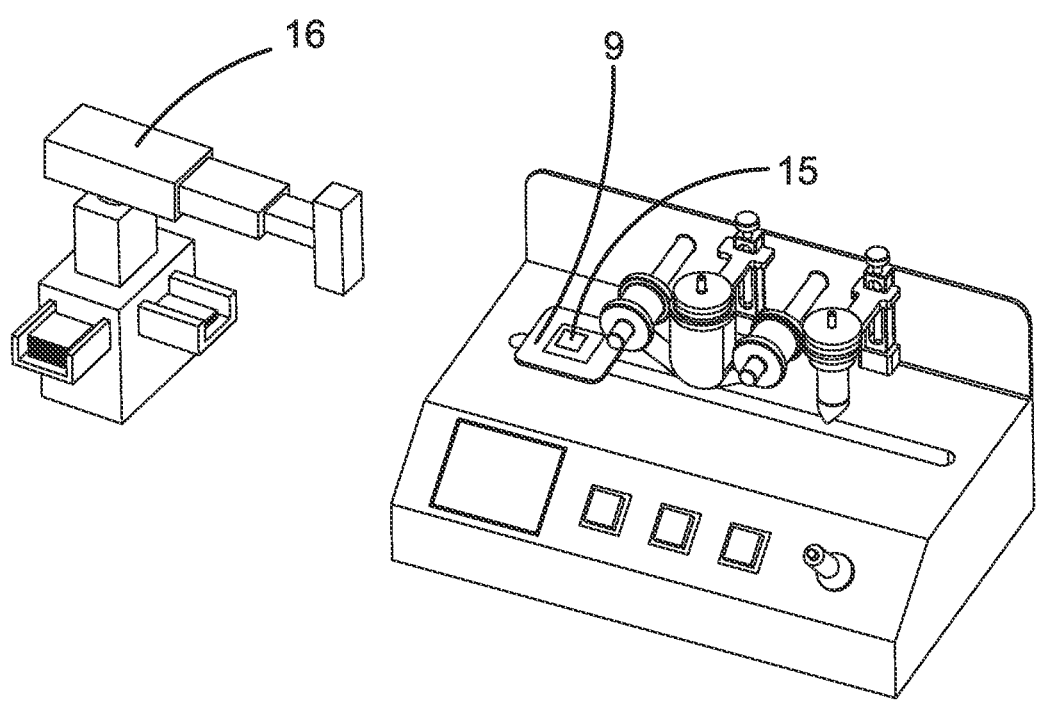
FIG. 4 illustrates a schematic view of lowering down a carrier of the film adhesion detection device of the present invention.
Figure 5:
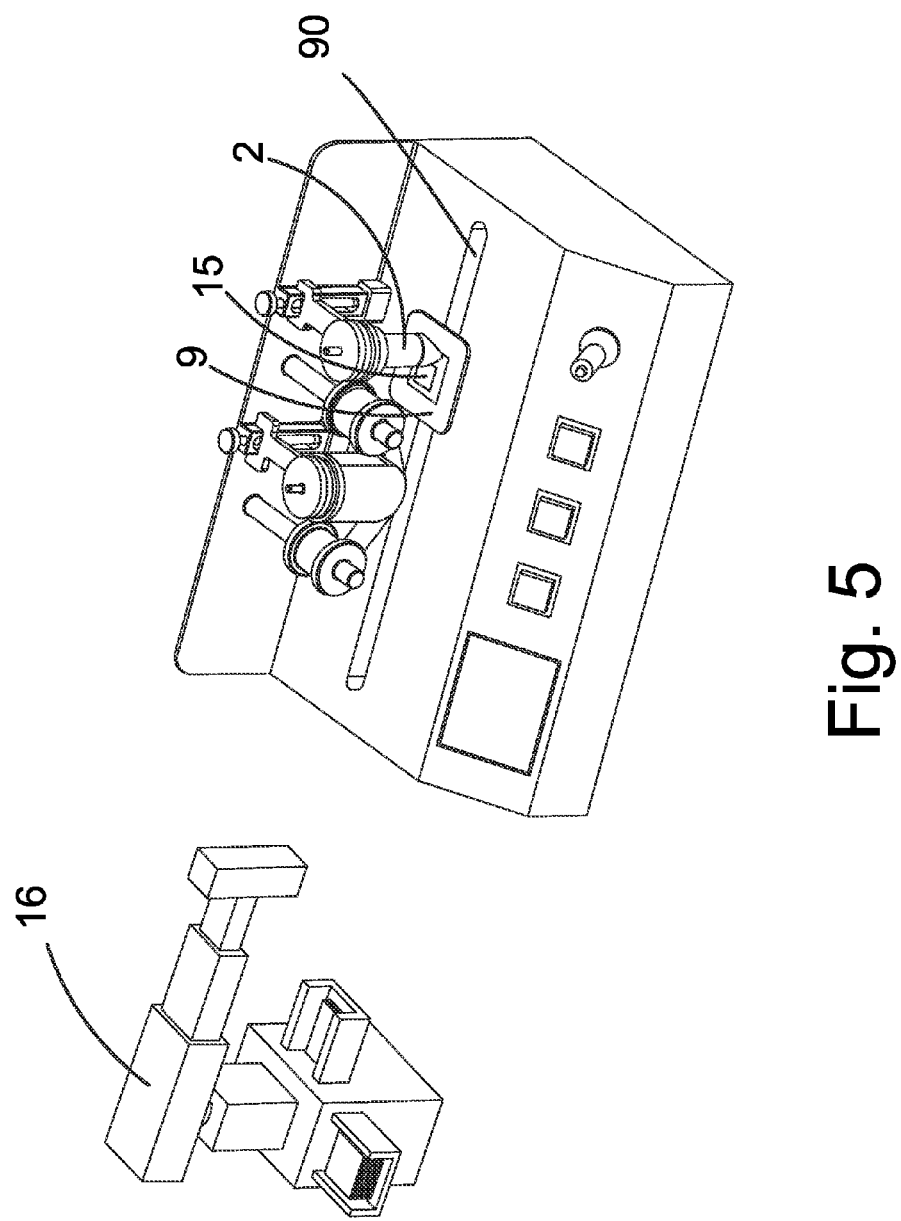
FIG. 5 illustrates a schematic view of right moving the carrier to a testing cutting tool of the film adhesion detection device of the present invention.
Figure 6:
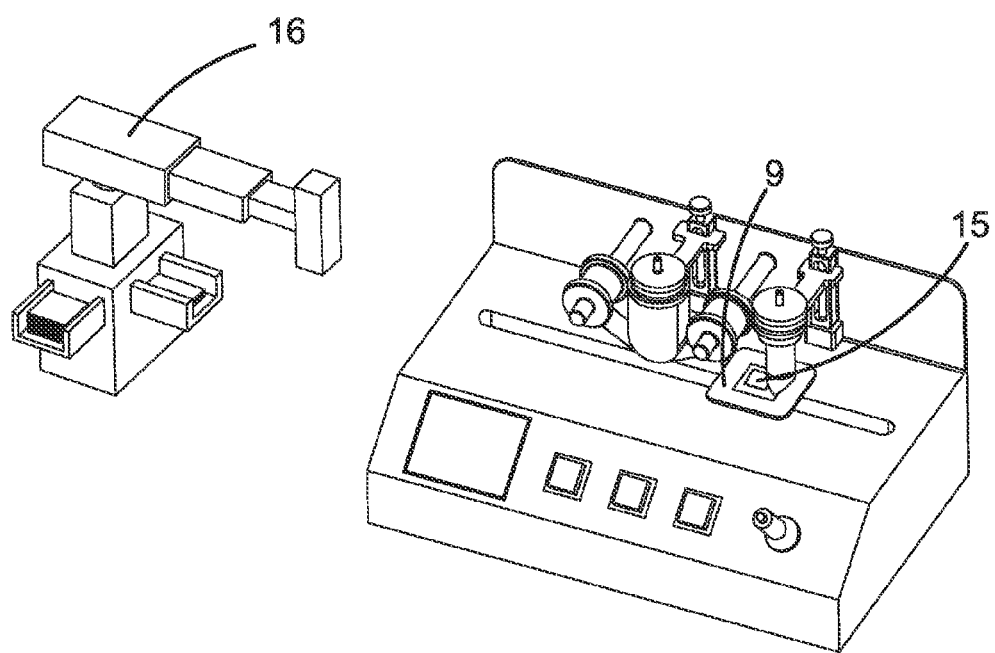
FIG. 6 illustrates a schematic view of raising up the carrier of the film adhesion detection device of the present invention.
Figure 7:
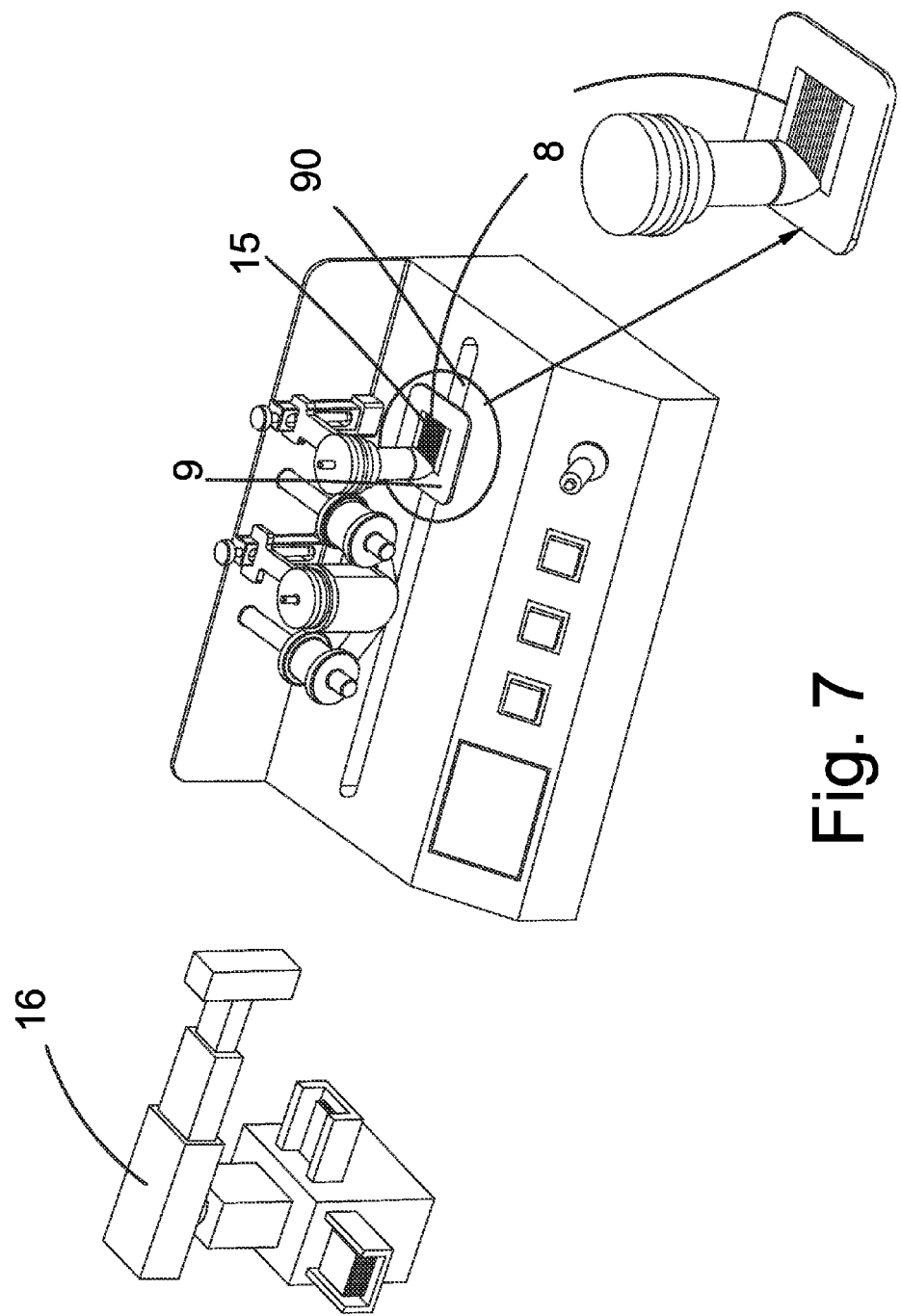
FIG. 7 illustrates a schematic view of proceeding an X-axis scratch test of the film adhesion detection device of the present invention.
Figure 8:
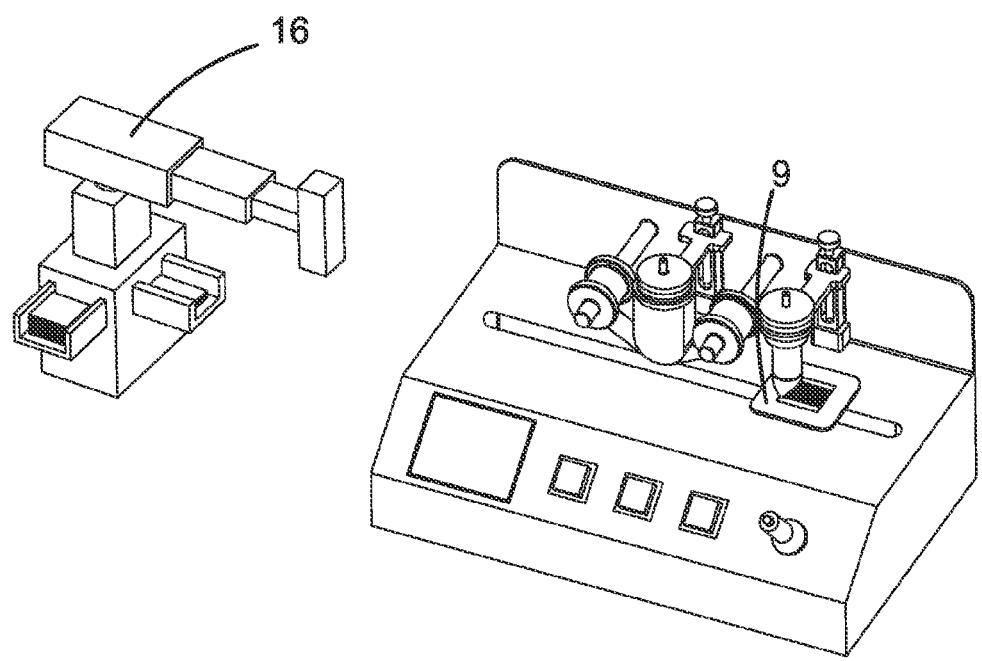
FIG. 8 illustrates a schematic view of lowering down the carrier of the film adhesion detection device of the present invention.
Figure 9:
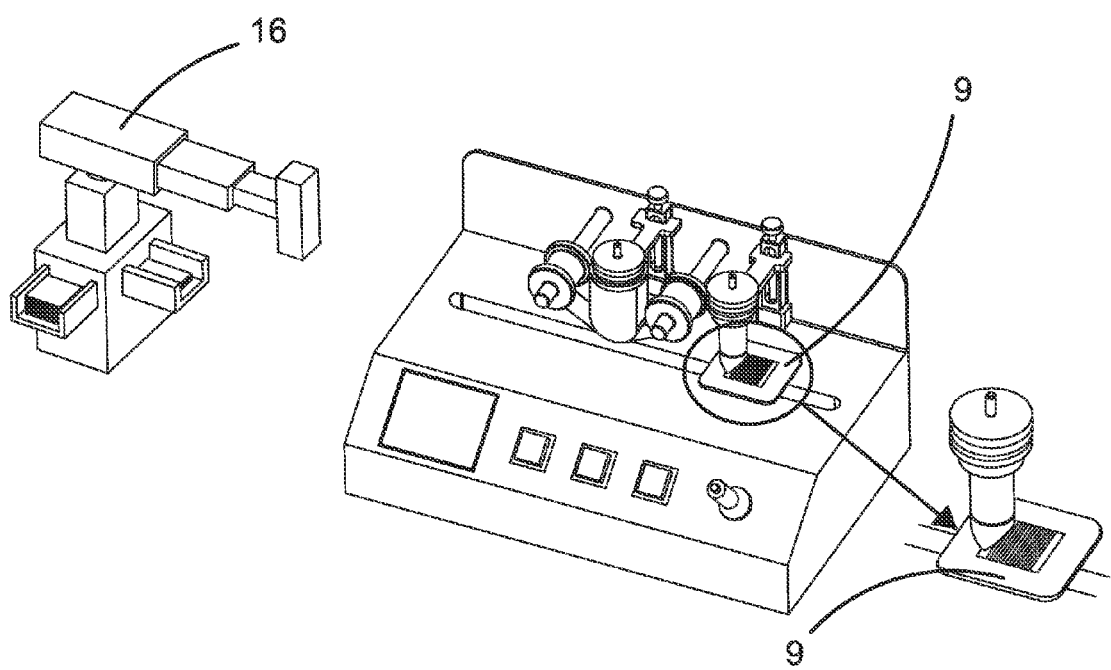
FIG. 9 illustrates a schematic view of rotating the carrier of the film adhesion detection device of the present invention.
Figure 10:
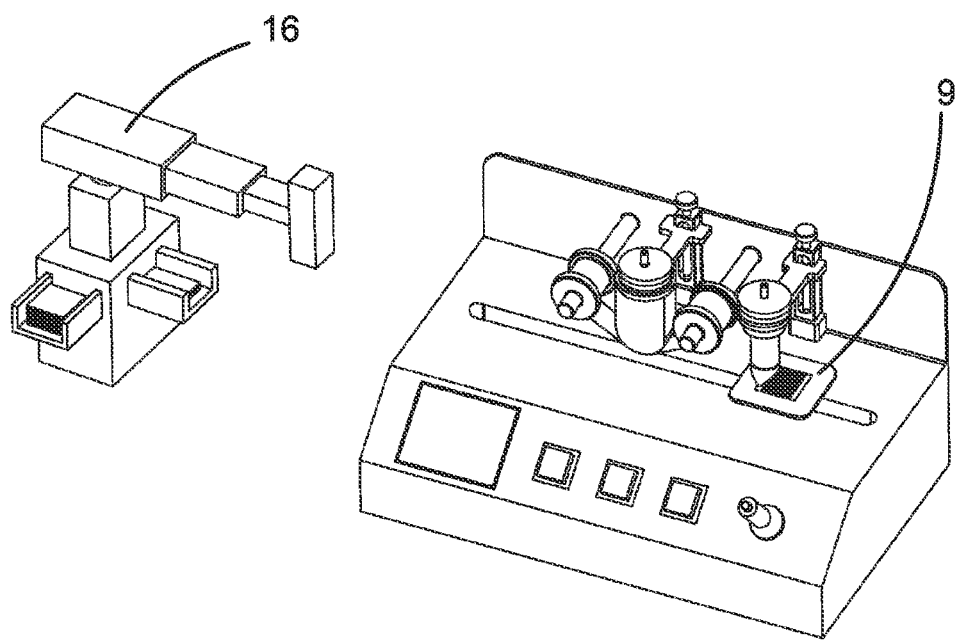
FIG. 10 illustrates a schematic view of raising up the carrier of the film adhesion detection device of the present invention.
Figure 11:
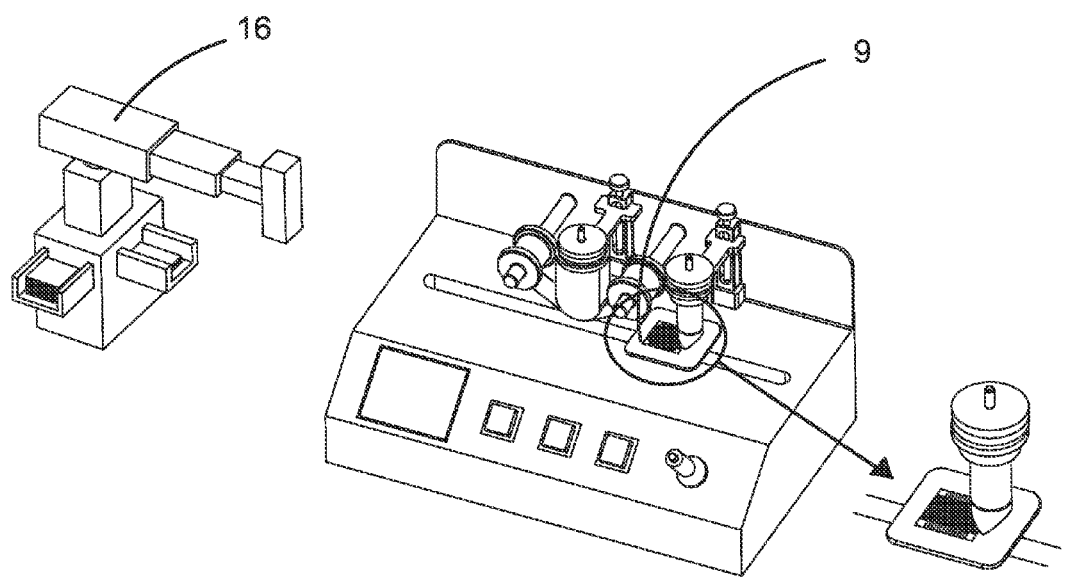
FIG. 11 illustrates a schematic view of left moving the carrier to proceed a Y-axis scratch test of the film adhesion detection device of the present invention.
Figure 12:
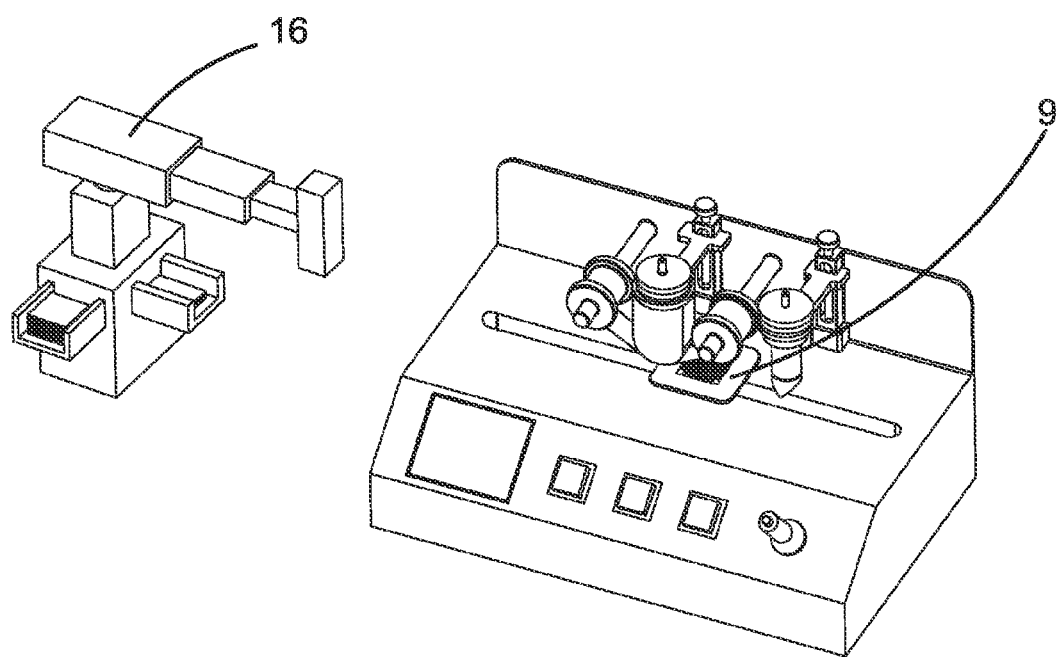
FIG. 12 illustrates a schematic view of starting to load a tape of the film adhesion detection device of the present invention.
Figure 13:
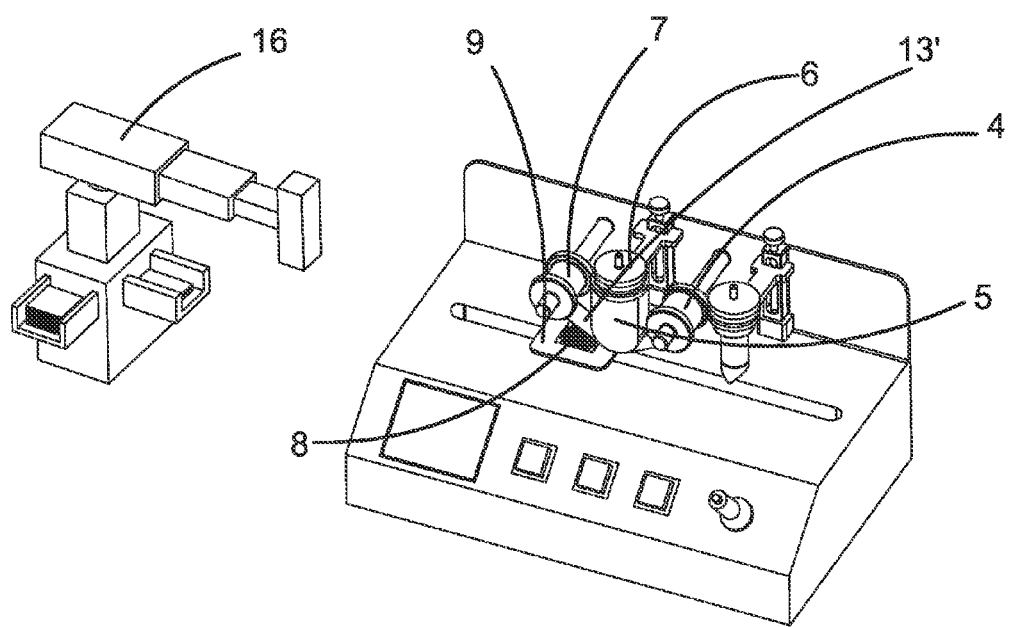
FIG. 13 illustrates a schematic view of finishing loading the tape of the film adhesion detection device of the present invention.
Figure 14:
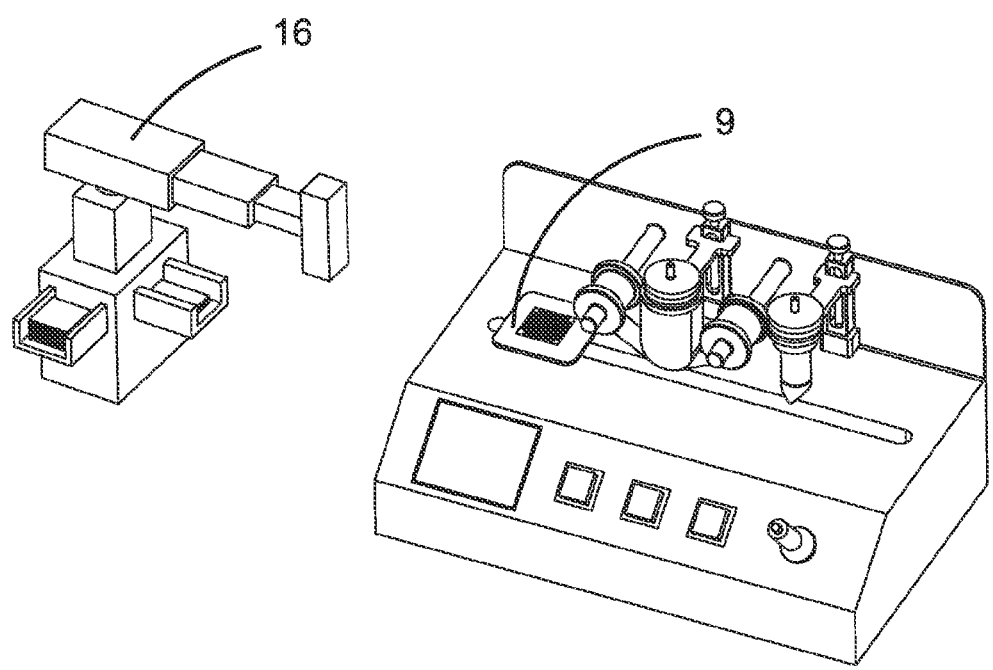
FIG. 14 illustrates a schematic view of returning the carrier of the film adhesion detection device of the present invention.
Figure 15:
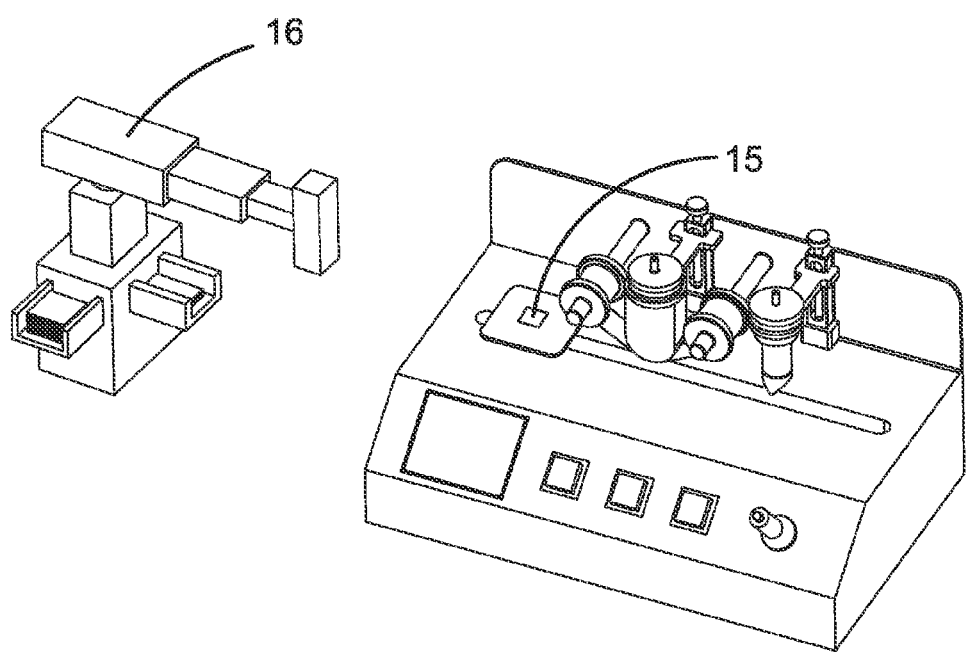
FIG. 15 illustrates a schematic view of unloading the testing sample of the film adhesion detection device of the present invention.
Figure 16:
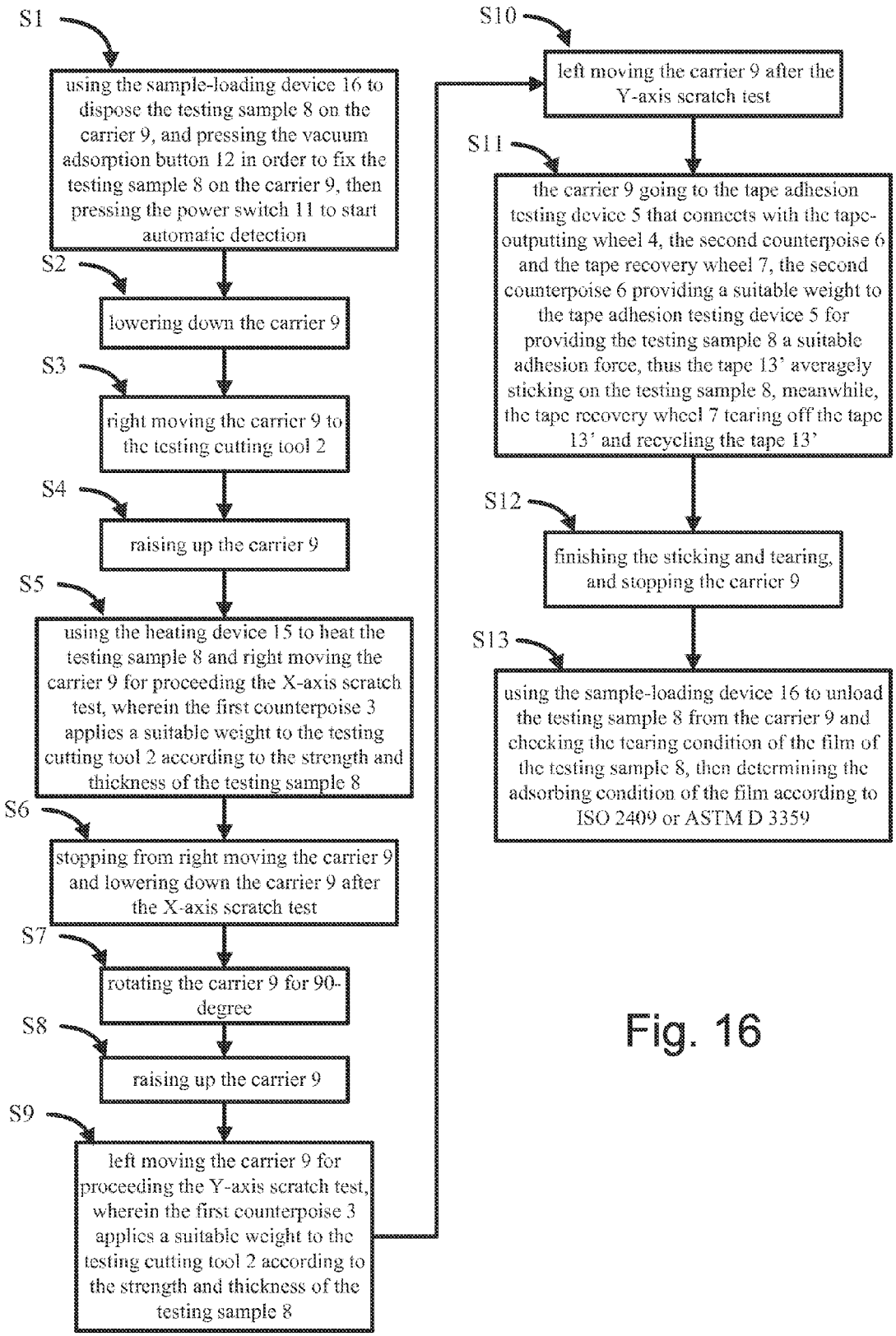
FIG. 16 illustrates a flow chart of the method for detecting the adhesion of a film using a film adhesion detection device of the present invention.

Please refer to FIG. 16, which illustrates a flow chart of the method for detecting the adhesion of a film using a film adhesion detection device of the present invention. Thus, to detect the adhesion of a film has the steps of:

(S1) using the sample-loading device 16 to dispose the testing sample 8 on the carrier 9, and pressing the vacuum adsorption button 12, which activates the vacuum means 19, which is associated with and under the carrier 9 and configured to create a suction in order to fix the testing sample 8 on the carrier 9, then pressing the power switch 11 to start automatic detection, as shown in FIG. 3;

(S2) lowering down the carrier 9, as shown in FIG. 4, since there is only a small distance for lowering down, FIG. 4 may not show very clearly;

(S3) right moving the carrier 9 along a guide slot 90 to the testing cutting tool 2, as shown in FIG. 5;

(S4) raising up the carrier 9, as shown in FIG. 6, since there is only a small distance for raising up, FIG. 6 may not show very clearly;

(S5) using the heating device 15 to heat the testing sample 8 and right moving the carrier 9 along a guide slot 90 for proceeding the X-axis scratch test, as shown in FIG. 7, including a magnify diagram to show the scratches formed in the testing sample 8 are in a parallel direction, wherein the first counterpoise 3 applies a suitable weight to the testing cutting tool 2 according to the strength and thickness of the testing sample 8;

(S6) stopping from right moving the carrier 9 and lowering down the carrier 9 after the X-axis scratch test, as shown in FIG. 8;

(S7) rotating the carrier 9 for 90-degree, as shown in FIG. 9;

(S8) raising up the carrier 9, as shown in FIG. 10, since there is only a small distance for raising up, FIG. 10 may not show very clearly;

(S9) left moving the carrier 9 for proceeding the Y-axis scratch test, as shown in FIG. 11, wherein the first counterpoise 3 applies a suitable weight to the testing cutting tool 2 according to the strength and thickness of the testing sample 8;

(S10) left moving the carrier 9 after the Y-axis scratch test, as shown in FIG. 12;

(S11) the carrier 9 going to the tape adhesion testing device 5 that connects with the tape-outputting wheel 4, the second counterpoise 6 and the tape recovery wheel 7, the second counterpoise 6 providing a suitable weight to the tape adhesion testing device 5 for providing the testing sample 8 a suitable adhesion force, thus the tape 13' averagely sticking on the testing sample 8, meanwhile, the tape recovery wheel 7 tearing off the tape 13' and recycling the tape 13', as shown in FIG. 13;

(S12) finishing the sticking and tearing, and stopping the carrier 9, as shown in FIG. 14; and (S13) using the sample-loading device 16 to unload the testing sample 8 from the carrier 9 and checking the tearing condition of the film of the testing sample 8, then determining the adsorbing condition of the film according to ISO 2409 or ASTM D 3359, as shown in FIG. 15.

While in the test, the testing sample 8 is able to fix on the carrier 9 via the vacuum adsorption button 12, and the carrier 9 is able to raise up and down, move back and forth, rotate, and position; further, the testing sample 8 may not be shaken due to the movement of the carrier 9, so the accuracy of the test may not be affected. Further, the testing sample 8 is pre-heated for proceeding the X-axis and Y-axis scratch tests, and either the high temperature of the testing sample 8 can be held to go to the tests or the testing sample 8 may be cooled down first, then go to the tests.

A condition of the present invention is described as follows. When the test sample 8 is in test and the carrier 9 right moves to the testing cutting tool 2 and raises up, a proper weight from the first counterpoise 3 is provided to the testing cutting tool 2 so as to proceed an X-axis scratch test. After that, the carrier 9 lowers down and turns 90-degree to go up in order to proceed a Y-axis scratch test. Continuously the carrier 9 starts a left movement again after finishing the Y-axis scratch test. As a mater of fact, according to the thickness of the film of the testing sample 8, a proper weight from the first counterpoise 3 can be provided, and therefore the testing cutting tool 2 can averagely apply a force on the testing sample 8, so as to reach the accuracy. The life of the testing cutting tool 2 is decayed with the increasing time of using the testing cutting tool 2. Hence, the testing cutting tool 2 is capable of dismantling so as to save cost and increase convenience.

Another condition of the present invention is described as follows. After finishing the scratch tests, the testing sample 8 goes to the tape adhesion testing device 5 that connects with the tape-outputting wheel 4, the second counterpoise 6 and the tape recovery wheel 7. The second counterpoise 6 provides a suitable weight to the tape adhesion testing device 5 for providing the testing sample 8 a suitable adhesion force, thus the tape 13 can averagely stick on the testing sample 8. Meanwhile, the tape recovery wheel 7 tears off the tape 13 and recycle the tape 13. Hence, the testing sample 8 is taken off so as to check the adsorbing condition of a film, so as to achieve time-saving and accuracy.

The present invention is going to test a film adhesion. And Not only the present invention can be automatic operated, but also can be manually operated for stepping operations.

As a conclusion, the film adhesion detection device provided by the present invention can effectively promote the added values thereof. The carrier is capable of raising up and down, moving back and forth, rotating, and positioning, so as to reach reality and convenience. The counterpoise and the dismantle testing cutting tool may provide a proper weight to the testing cutting tool for the testing cutting tool averagely applying a force on the testing sample and rapidly dismantling the testing cutting tool if it is damaged due to abrasion, so that saving time and the cost of the testing cutting tool will be approached. Further, the tape adhesion testing device that connects with the tape-outputting wheel, the counterpoise and the tape recovery wheel. The counterpoise provides a suitable weight to the tape adhesion testing device, thus the test for adhering and tearing off the tape is finished soon, and the tape can be recycled.

Although the invention has been disclosed and illustrated with reference to particular embodiments, the principles involved are susceptible for use in numerous other embodiments that will be apparent to persons skilled in the art. This invention is, therefore, to be limited only as indicated by the scope of the appended claims

What is claimed is:

1. A film adhesion detection device comprising:
   a testing member, comprising:
   a carrier having vacuum means and a heating device, the vacuum means for fixing a testing sample onto the carrier, and the heating device for heating the testing sample, the carrier being under controlled of a handhold rod to move back and forth along a guide slot of the testing member, raise up and down, rotate and position, the guide slot being along an X axial direction;
   a testing cutting tool installed at a moving path of the carrier having a plurality of sets of knives to generate a plurality of parallel scratches on the testing sample along the X axial direction;
   a first counterpoise providing a predetermined weight for a particular strength and thickness of the testing sample applying onto the testing cutting tool;
   a tape adhesion testing device installed at the moving path of the carrier having a tape-outputting wheel, a second counterpoise and a tape-recovery wheel, the tape-outputting wheel provided to paste a tape on the testing sample having the scratches formed therein, and the second counterpoise providing an adhesion force onto the testing sample having the tape pasted thereon, and the tape-recovery wheel provided to recycle the tape by peeling off the tape from the testing sample;
   and a sample-loading device, provided to unload the testing sample onto the carrier, or upload the testing sample from the carrier.

2. A method for detecting the adhesion of a film using a film adhesion detection device comprising the steps of:
   (S1) using a sample-loading device to dispose a testing sample on a carrier of a testing member of a film adhesion detection device and fix the testing member onto the carrier by a vacuum suction;
   (S2) lowering down the carrier;
   (S3) moving the carrier to a testing cutting tool;
   (S4) raising up the carrier;
   (S5) heating the testing sample by a heating device, and then applying a predetermined weight by a first counterpoise onto a testing cutting tool, which has a plurality of knives and then moving the carrier against the testing cutting tool so as to generate a plurality of first parallel scratches into the testing sample and then lowering down the carrier;
   (S6) lowering down the carrier;
   (S7) rotating the carrier by an angle of 90°;
   (S8) raising up the carrier;
   (S9) reversely moving the carrier against the testing cutting tool to generate a plurality of second parallel scratches into the testing sample and then lowering down the carrier;
   (S10) moving the carrier to a tape adhesion testing device having a tape-outputting wheel, a second counterpoise and a tape-recovery wheel;
   (S11) performing a tape adhesion test by pasting a tape on the testing sample through the tape-outputting wheel and providing an adhesion force onto the testing sample with a predetermined weight by using the second counterpoise, and then recycling the tape on the testing sample by using the tape-recovery wheel, and
   (S12) determining an adsorbing condition of the film in accordance with the film cells peeled off by the tape wherein the film cells are the cells due to the first parallel scratches along an X axial direction and the second parallel scratches.

3. The method for detecting the adhesion of a film method for detecting the adhesion of a film using a film adhesion detection device according to the claim 2, wherein the determination of the adsorbing condition of the film is based on ISO 2409:2013 or ASTM D 3359 09E2.

* * * * *